United States Patent [19]

Shirley et al.

[11] Patent Number: 5,532,384

[45] Date of Patent: Jul. 2, 1996

[54] PROCESS FOR PRODUCING HYDROCARBON PARTIAL OXIDATION PRODUCTS

[75] Inventors: Arthur Shirley, Piscataway; Ramakrishnan Ramachandran, Allendale, both of N.J.

[73] Assignee: The BOC Group, Inc., New Providence, N.J.

[21] Appl. No.: 239,636

[22] Filed: May 9, 1994

Related U.S. Application Data

[63] Continuation-in-part of Ser. No. 934,049, Aug. 21, 1992, abandoned.

[51] Int. Cl.⁶ .................................................. C07D 307/30
[52] U.S. Cl. ....................... 549/257; 549/258; 549/261; 549/262
[58] Field of Search ......................... 549/257, 258, 549/261, 262

[56] References Cited

U.S. PATENT DOCUMENTS

| | | |
|---|---|---|
| 4,259,246 | 3/1981 | Bakshi et al. . |
| 4,342,699 | 8/1982 | Palmer et al. . |
| 4,868,330 | 9/1989 | Ramachandran et al. . |
| 4,987,239 | 1/1991 | Ramachandran et al. ............. 549/262 |

Primary Examiner—Johann Richter
Assistant Examiner—John Peabody
Attorney, Agent, or Firm—Coleman R. Reap; Larry R. Cassett

[57] ABSTRACT

Hydrocarbon derivatives are produced by contacting a hydrocarbon with oxygen obtained from an air separation unit in the presence of a partial oxidation reaction catalyst. After separation of the hydrocarbon derivative from the reactor effluent, unreacted hydrocarbon is recovered from the effluent by adsorbing the unreacted hydrocarbon onto an adsorbent at superatmospheric pressure and removing the adsorbed hydrocarbon from the adsorbent by depressurizing said adsorbent and purging the adsorbent with nitrogen obtained from the air separation unit. The recovered unreacted hydrocarbon is recycled to the partial oxidation reactor.

8 Claims, 1 Drawing Sheet

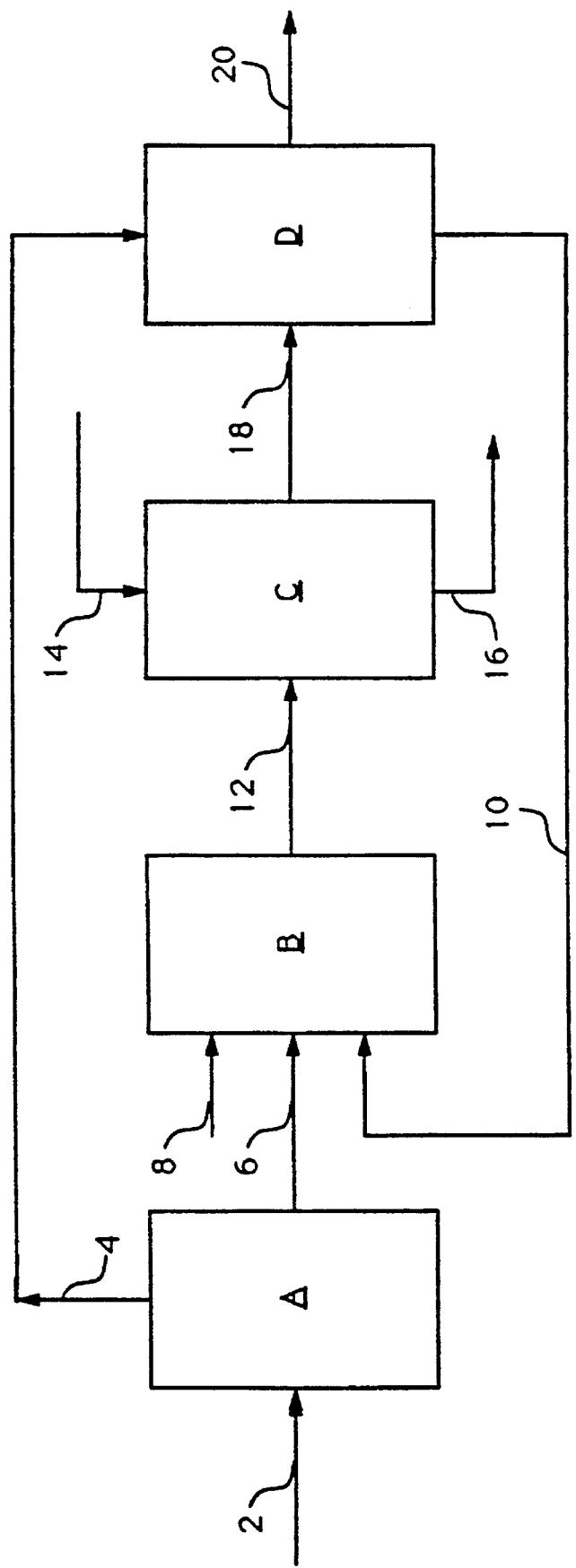

PROCESS FOR PRODUCING HYDROCARBON PARTIAL OXIDATION PRODUCTS

RELATED APPLICATIONS

This application is a continuation-in-part of application Ser. No. 07/934,049, filed Aug. 21, 1992, now abandoned.

BACKGROUND OF THE INVENTION

This invention relates to the production of hydrocarbon derivatives by the partial oxidation of hydrocarbons, and more particularly to the use of air separation products in a recycle partial oxidation process.

Certain partial oxidation products are produced commercially by the oxidation of an appropriate hydrocarbon in the vapor phase over a suitable catalyst. For example, maleic anhydride is produced commercially by the vapor phase catalytic partial oxidation of aromatic hydrocarbons, such as benzene, or straight-chain hydrocarbons, such as n-butane or butene, in the presence of an oxygen-containing gas, over a vanadium-containing catalyst. Similarly, nitriles, alkylene oxides, aldehydes and halogenated hydrocarbons are produced by the partial oxidation of appropriate alkanes and alkenes in the presence of selected catalysts. Air has generally been used as the oxygen-containing gas, because of its low cost and ready availability. The reaction can be carried out in any suitable reactor, and the effluent from the reactor generally contains be carried out in any suitable reactor, and the effluent from the reactor generally contains the partial oxidation product, carbon dioxide ($CO_2$), carbon monoxide (CO), water, unreacted hydrocarbon and smaller amounts of other partially oxidized byproducts.

The reaction equipment train generally consists of a reactor, in which the partial oxidation product is produced, a scrubber, in which the partial oxidation product is scrubbed from the reactor effluent gases by means of water or other solvent for the partial oxidation product, and means for further treating the scrubbed effluent gases. In modern recycle processes means are also provided for removing unreacted hydrocarbons from the scrubbed gas stream and recycling them to the partial oxidation reactor.

Adsorption systems are often used for removing unreacted hydrocarbons from scrubbed partial oxidation gaseous effluents. When used for such purpose the system generally contains an adsorbent which preferentially adsorbs unreacted hydrocarbon from the scrubbed gas stream. When the system is designed properly it adsorbs the unreacted hydrocarbons without also adsorbing excessive amounts of the other components of the gas stream, such as nitrogen, argon, carbon dioxide and carbon monoxide.

When temperature swing adsorption (TSA) systems are used for the removal of the unreacted hydrocarbon from offgas streams from partial oxidation reactors, the adsorption beds are generally regenerated by passing a heated nonadsorbable or weakly adsorbable purge gas through the bed. The purge gas desorbs the adsorbed components from the bed and sweeps them out of the system. U.S. Pat. No. 4,231,943 discloses a TSA process for the production of maleic anhydride by the partial oxidation of n-butane. In the process disclosed in this patent a portion of the n-butane-containing off gas from the product gas scrubber is recycled directly to the partial oxidation reactor, and the remainder is passed through an adsorption drum wherein butane is adsorbed from the offgas. The n-butane is desorbed from the adsorption bed by purging the bed with heated nitrogen or a nitrogen-air mixture. The n-butane-purge gas mixture is recycled to the partial oxidation reactor. Federal Republic of Germany Patent Disclosure 25 44 972 likewise discloses a partial oxidation reaction process for producing maleic anhydride in which unreacted $C_4$ hydrocarbons are recovered from the reactor offgas by temperature swing adosrption. In this patent the adsorption bed is purged with heated air.

The present invention provides a process which provides advantages over the above-described processes.

SUMMARY OF THE INVENTION

According to a broad embodiment of the invention, a recycle partial oxidation reaction is carried out by reacting a hydrocarbon with oxygen-rich product (defined below) to produce a selected partial oxidation product; the selected product is removed from the gaseous reactor effluent; the gaseous effluent is passed through an adsorber at superatmospheric pressure, thereby adsorbing unreacted hydrocarbon from the effluent; the unreacted hydrocarbon is desorbed from the adsorption bed by depressurizing the bed; the bed is purged by passing a stream of nitrogen-rich product (defined below) through the bed; and the desorbed unreacted hydrocarbon-nitrogen-rich product mixture is recycled to the partial oxidation reactor.

In a preferred embodiment, air is passed through an air separation system, thereby separating the air into nitrogen-rich product and oxygen-rich product; the oxygen-rich product is used as the oxidant in a hydrocarbon partial oxidation process in which unreacted hydrocarbon is separated from the gaseous effluent from the partial oxidation product recovery unit by passing the effluent through an adsorber at superatmospheric pressure, thereby adsorbing unreacted hydrocarbon from the effluent; the unreacted hydrocarbon is desorbed from the adsorption bed by depressurizing the bed, the bed is purged by passing a stream of nitrogen-rich product through the bed; and the desorbed unreacted hydrocarbon-nitrogen-rich product mixture is recycled to the partial oxidation reactor.

BRIEF DESCRIPTION OF THE DRAWING

The preferred embodiment of the invention is illustrated in the drawing, which is a schematic representation of a recycle partial oxidation reaction system.

DETAILED DESCRIPTION OF THE INVENTION

The process of the invention can be used for the manufacture of any petrochemical that is produced by the gas phase reaction at elevated temperatures of a hydrocarbon with oxygen. Typical petrochemical manufacturing processes in which the invention can be employed are:

The manufacture of cyclic anhydrides by the reaction of aromatic compounds or straight-chained $C_4$ hydrocarbons with oxygen in the presence of a vanadia-based catalyst. Examples include the production of maleic anhydride by the reaction of benzene or a saturated or unsaturated $C_4$ hydrocarbon with oxygen and the manufacture of phthalic anhydride by the reaction of o-xylene or naphthalene with oxygen.

The manufacture of alkylene oxides by the reaction of lower alkanes or alkenes with oxygen in the presence of a silver oxide catalyst mounted on a silica or alumina support. Examples include the reaction of ethane or ethylene with oxygen to produce ethylene oxide and the reaction of propane or propylene with oxygen to produce propylene oxide.

The manufacture of chlorinated hydrocarbons by the reaction of lower alkanes or alkenes with oxygen in the presence of a copper chloride catalyst supported on silica or alumina. Examples include the reaction of ethylene or ethane with hydrogen chloride to produce vinyl chloride or ethylene dichloride.

The manufacture of an olefinically unsaturated nitriles by the reaction of lower alkanes or alkenes with oxygen and ammonia in the presence of a bismuth molybdenum oxide catalyst or an iron antimony oxide catalyst mounted on a silica or alumina support. Examples of this type of process include the reaction of propane or propylene with oxygen to produce acrylonitrile and the reaction of i-butane or i-butylene with oxygen to produce methacrylonitrile.

The particular hydrocarbon used in the feed will, of course, depend upon which petrochemical is to be produced. When cyclic anhydrides are to be produced, the hydrocarbon reactant is usually a low molecular weight aromatic hydrocarbon, i.e. one containing up to 12 carbon atoms, or a low molecular weight straight-chain hydrocarbon, i.e. one containing up to 10 carbon atoms. When olefinically unsaturated nitriles, alkylene oxides, chlorinated hydrocarbons or are to be produced, the hydrocarbon reactant is usually a low molecular weight alkane or alkene, i.e. one containing up to 10 carbon atoms.

The apparatus used in the process of the invention and the arrangement of the various units in the overall system of the invention are illustrated in the accompanying drawing. The equipment units used in the preferred embodiment include an air separation system, A, a hydrocarbon partial oxidation reactor, B, a petrochemical product recovery unit, C, and a pressure swing adsorption system, D.

Air separation unit A can be any system which separates nitrogen and oxygen from air. Typical air separation devices useable in the process of the invention are cryogenic fractional distillation systems, adsorption systems and semipermeable membrane systems. When unit A is a cryogenic distillation system it can be a simple one-column unit, a two-column unit having high pressure and a low pressure columns or a two-column unit with an argon sidearm column. Similarly, when unit A is an adsorption system, it may be any type of adsorption system, such as a simple adsorption system which is regenerated by means of a purge gas, a pressure swing adsorption (PSA) system, a temperature swing adsorption (TSA) system or combinations of these. In preferred embodiments of the invention, unit A is a cryogenic distillation system or a PSA system.

Reactor B may be any suitable partial oxidation reactor and it may be equipped with heat exchange means (not shown) to remove heat developed in the reaction, which is exothermic. Reactor B may be packed with a catalyst suitable for the specific partial oxidation reaction being carried out.

Hydrocarbon derivative recovery unit C may be any conventional device for removing a hydrocarbon derivative from a gaseous stream, such as a gas scrubber, i.e. an absorber, or a condenser. In the drawing it is illustrated as a scrubber with means for contacting the product gas with water or an aqueous or nonaqueous liquid to extract the petrochemical product from the reactor effluent and means for withdrawing the scrubbed petrochemical from the recovery unit.

As indicated above, separator D is a pressure swing adsorption (PSA) system. It may comprise a single adsorption bed or a battery of beds arranged in series or parallel or in combinations of these. In preferred plants the PSA system comprises two or more adsorbent beds cycled out of phase to provide a pseudo-continuous recycle of unreacted hydrocarbon to reactor B. Preferred PSA plants comprise two or more beds operated in a cyclic process comprising adsorption under relatively high pressure and desorption or bed regeneration under relatively low pressure or vacuum.

The function of Separator D is to adsorb unreacted hydrocarbons from partial oxidation waste gas streams, which generally contain unreacted hydrocarbons; partial oxidation byproducts; such as carbon dioxide, water vapor and carbon monoxide; and various other gaseous components, such as nitrogen, argon and small amounts of oxygen. Hydrocarbons are generally more strongly adsorbed by most adsorbents than are the other components of the unit C effluent; accordingly, unit D contains an adsorbent which more strongly adsorbs hydrocarbons than the other components of the waste gas streams. Typical of the adsorbents useful in unit D are zeolite molecular sieves, activated carbon, carbon molecular sieves, silica gel, activated alumina, etc.

The above-described units of equipment are all well known and their design features do not constitute a part of the present invention.

In the process of the invention as practiced in the embodiment illustrated in the drawing, air separation unit A receives a feed stream of air through line 2 and discharges nitrogen-rich product through line 4 and oxygen-rich product through line 6.

The nitrogen-rich product is used as a purge gas to sweep unreacted hydrocarbon from separator D; accordingly, it may be substantially pure nitrogen, a mixture of nitrogen and argon or nitrogen-enriched air, provided that the oxygen content of the nitrogen-enriched air is not high enough to create a flammable gas mixture with the desorbed hydrocarbon at any point in the recycle line. The composition of the nitrogen-rich product will depend to a considerable extent upon the method used to separate the air components. For purposes of this invention "nitrogen-rich product" is defined as substantially pure nitrogen or a nitrogen-rich air derivative the oxygen content of which is insufficient to cause a flammable mixture to be formed in the recycle section of the system of the invention. In other words, the oxygen introduced into separator D as part of the nitrogen-rich product purge stream will not be sufficient to produce a flammable mixture when combined with the desorbed gas component(s) exiting separator D. In the preferred embodiment of the invention the nitrogen-rich product is substantially pure nitrogen.

The oxygen-rich product may be substantially pure oxygen or it may contain argon or be oxygen-enriched air, and its composition will depend on the particular air separation device used in the process of the invention. For purposes of the invention, "oxygen-rich product" is defined as substantially pure oxygen or an oxygen-rich air derivative containing at least 80 volume percent oxygen.

It is usually preferred to use substantially pure oxygen in the partial oxidation reaction since the efficiency of the reaction decreases as the concentration of inert gases such as nitrogen or argon increases. However, in some cases it may be desirable to use lower purity oxygen than is available from air separation units. This can be accomplished by mixing air with the oxygen-rich product obtained from the air separation unit or by introducing both oxygen-rich product and air into reactor B, provided that the total oxygen concentration of the combined oxygen-rich product and supplemental air is not lower than about 80 volume percent.

The oxygen-rich product leaving unit A flows into hydrocarbon partial oxidation reactor B through line 6. Reactor B receives, in addition to the oxygen-rich product, a hydrocarbon feed through line 8 and a recycle stream through line 10. Other reactants, such as ammonia, hydrogen chloride, chlorine, etc., which are required when products such as nitriles, chlorinated hydrocarbons, etc. are to be produced are introduced into reactor B through feed lines that are not shown in the drawing. Reaction moderating agents, such as carbon dioxide or other inert gases can also be introduced into unit B with the reactants.

As an alternative to the reactor B reactant feed arrangement illustrated in the drawing, some or all of the reactants, including the unreacted hydrocarbon contained in the recycle stream, can be premixed and introduced together into reactor B, if desired, provided that such mixing does not create a fire or explosion hazard. The particular inlet arrangement will generally depend upon the type of reactor used for practicing the invention. In fixed bed reactor systems the components of the feed are generally mixed before they enter the reactor and are thus fed into the reactor through a single line, whereas in fluidized bed reactor systems, the components are usually separately fed into the reactor. The specific details of the partial oxidation reaction and the method of introduction of the reactants into reactor B forms no part of the invention.

The components entering reactor B contact the catalyst in reactor B and react to produce the petrochemical product and carbon dioxide and carbon monoxide byproducts. The conditions of the hydrocarbon oxidation reaction are well known and form no part of the invention. Typically, the oxidation reaction is conducted at a temperature of from about 200° to 600° C., and usually from about 250° to 500° C., and at pressures typically in the range of from about 2 to 500 psig, and usually from about 3 to 300 psig. The reactants are generally passed through the reactor at a velocity in the range of from about 0.5 to 5.0 ft/sec. The ratio of oxygen to hydrocarbon in the feed is suitably in the range of 0.3:1 to 10:1 by volume.

The partial oxidation reaction product stream leaves reactor B through line 12 and is usually cooled to a temperature in the range of about 30° to about 200° C. by passage through a heat exchanger (not shown). After being cooled the product gas stream enters product recovery unit C, in which the petrochemical product is removed from the gas stream. In recovery unit 8 the product gases are intimately contacted with a solvent which enters this unit through line 14. The solvent dissolves substantially all of the desired petrochemical in the product gas stream and the petrochemical-containing solution exits product recovery unit C via line 16. It is usually further treated to recover the petrochemical product. The scrubbed gas stream leaves recovery unit C through line 18. The entire gaseous effluent from unit C is compressed to a superatmospheric pressure and passed to separator D.

As the gaseous effluent from unit C passes through separator D substantially all of the unreacted hydrocarbon is adsorbed by the adsorbent contained therein. The nonadsorbed gases leave separator D through waste gas discharge line 20 and can be vented to the atmosphere or otherwise disposed of. When the unreacted hydrocarbon front reaches a predetermined point in saparator D, the flow of feed gas to separator D is terminated and the regeneration phase of the cycle is begun. During this phase the adsorber is counter-currently depressurized. During at least part of the adsorbent regeneration phase of the adsorption cycle nitrogen-rich product from air separation unit A passes through line 4 and is introduced into separator D at low pressure as a purge gas. The nitrogen-rich product assists in the desorption of unreacted hydrocarbons from the adsorbent bed, and the unreacted nitrogen-rich gas-hydrocarbon mixture passes out of separator D and is recycled to reactor B through line 10.

The adsorption cycle may contain steps other than the fundamental steps of adsorption and regeneration. For example, it may be advantageous to depressurize the adsorption bed in two steps, with the first depressurization product being used to partially pressurize another bed in the adsorption system. This will reduce the amount of nonhydrocarbon gases recycled to the reactor with the unreacted hydrocarbon.

Several advantages are realized by use of the invention. The components of air are used in the process in the parts of the system where they are most useful. The oxygen-rich product component is used as the oxidant, accordingly energy is not wasted heating the large quantity of nitrogen that accompanies the required volume of oxygen when air is used as the oxidant. Secondly, nitrogen-rich product is used as purge gas; accordingly there is little or no risk of creating an explosive gas mixture hazard in the gas separation system. Thirdly, the nitrogen that is introduced into the reactor in the recycle stream serves as an inert diluent. The volume of nitrogen entering reactor B can be increased, if desired by increasing the amount of nitrogen passed through separator D as purge gas. If desired, additional amounts of nitrogen can be introduced into reactor B by adjusting the concentration of nitrogen in the oxygen-rich product stream or by introducing air into the reactor in addition to the oxygen-rich product. Lastly, since all of the effluent from the petrochemical recovery unit is passed through the unreacted hydrocarbon PSA recovery system, the amount of inert gases and byproduct gases recycled to the partial oxidation reactor is minimized.

Although the invention has been described with particular reference to the system illustrated in the drawing, variations are contemplated. For example, the invention can be used with any reaction between a gaseous material and oxygen in which it is desired to recover and recycle unreacted portions of the gaseous material, provided that an adsorbent can be found that adsorbs the unreacted gaseous material more strongly than the other gaseous components of the reactor effluent. The scope of the invention is limited only by the breadth of the appended claims.

We claim:

1. In a process for the production of a hydrocarbon derivative selected from cyclic anhydrides, alkylene oxides, halogenated hydrocarbons, aldehydes, unsaturated carboxylic acids, unsaturated nitriles and mixtures of these comprising:

(a) contacting in the vapor phase in a reaction zone at a temperature in the range of about 200° to about 600° C. a hydrocarbon containing 2 to 12 carbon atoms and oxygen in the presence of a catalyst which catalyzes the partial oxidation of said hydrocarbon to the selected hydrocarbon derivative, thereby producing a gaseous product stream containing said hydrocarbon derivative;

(b) removing said hydrocarbon derivative from said gaseous product stream;

(c) flowing substantially all of the hydrocarbon derivative-free gaseous product stream from step (b) at superatmospheric pressure through an adsorption bed containing an adsorbent which is selective for said hydrocarbon, thereby removing unreacted hydrocarbon from said hydrocarbon derivative-free gaseous product stream; and (d) terminating the flow of hydrocarbon derivative-free gaseous product stream through said adsorption bed when the unreacted hydrocarbon front reaches a predetermined point in said adsorption bed, and depressurizing said adsorption bed, thereby desorbing unreacted hydrocarbon from said adsorption bed; the improvement comprising:

(e) passing nitrogen-rich product through said adsorption bed, thereby further desorbing unreacted hydrocarbon from said adsorption bed; and (f) recycling desorbed unreacted hydrocarbon and nitrogen-rich product to said reaction zone.

2. In a process for the production of a hydrocarbon derivative selected from cyclic anhydrides, alkylene oxides, halogenated hydrocarbons, aldehydes, unsaturated carboxylic acids, unsaturated nitriles and mixtures of these comprising:

contacting in the vapor phase in a reaction zone at a temperature in the range of about 200° to about 600° C. a hydrocarbon containing 2 to 12 carbon atoms and oxygen-containing gas in the presence of a catalyst which catalyzes the partial oxidation of said hydrocarbon to the selected hydrocarbon derivative, thereby producing a gaseous product stream containing said hydrocarbon derivative;

(b) recovering substantially all of said hydrocarbon derivative from said gaseous product stream;

(c) flowing substantially all of the hydrocarbon derivative-free gaseous product stream from step (b) at superatmospheric pressure through an adsorption bed containing an adsorbent which is selective for said hydrocarbon, thereby removing unreacted hydrocarbon from said hydrocarbon derivative-free gaseous product stream; and (d) terminating the flow of hydrocarbon derivative-free gaseous product stream through said adsorption bed when the unreacted hydrocarbon front reaches a predetermined point in said adsorption bed, and depressurizing said adsorption bed, thereby desorbing unreacted hydrocarbon from said adsorption bed; the improvement comprising:

(e) separating air into oxygen-rich product and nitrogen-rich product;

(f) using said oxygen-rich product in step (a) as said oxygen-containing gas;

(g) passing nitrogen-rich product through said adsorption bed, thereby further desorbing unreacted hydrocarbon from said adsorption bed; and (h) (g) recycling the desorbed unreacted hydrocarbon to said reaction zone.

3. The process of claim 2, wherein step (e) is carried out by cryogenic fractional distillation.

4. The process of claim 2, wherein step (e) is carried out by pressure swing adsorption.

5. The process of any one of claims 1 to 4, wherein said oxygen-rich product is substantially pure oxygen.

6. The process of any one of claims 1 to 4, wherein said nitrogen-rich product is substantially pure nitrogen.

7. The process of claim 1 or claim 2, wherein said hydrocarbon is selected from aromatic hydrocarbons containing 6 to 12 carbon atoms and aliphatic hydrocarbons containing 2 to 10 carbon atoms.

8. The process of claim 1, wherein said hydrocarbon derivative is a cyclic anhydride.

* * * * *